United States Patent [19]
Nair et al.

[11] Patent Number: 6,121,315
[45] Date of Patent: Sep. 19, 2000

[54] ORAL COMPOSITIONS CONTAINING A ZINC COMPOUND

[75] Inventors: Mona Nair; Pauline Pan, both of Morris Plains; Lori Kumar, Skillman, all of N.J.

[73] Assignee: Warner-Lambert Company, Morris Plains, N.J.

[21] Appl. No.: 09/269,256

[22] PCT Filed: Sep. 19, 1997

[86] PCT No.: PCT/US97/16735

§ 371 Date: Mar. 19, 1999

§ 102(e) Date: Mar. 19, 1999

[87] PCT Pub. No.: WO98/11867

PCT Pub. Date: Mar. 26, 1998

Related U.S. Application Data

[60] Provisional application No. 60/027,435, Sep. 20, 1996.

[51] Int. Cl.⁷ ......................... A61K 31/315; A61K 7/16
[52] U.S. Cl. ............................. 514/494; 514/901; 424/49
[58] Field of Search .............................. 424/49; 514/494, 514/901

[56] References Cited

U.S. PATENT DOCUMENTS

| | | | |
|---|---|---|---|
| 3,111,127 | 11/1963 | Jarboe et al. | 131/17 |
| 4,022,880 | 5/1977 | Vinson et al. | 424/49 |
| 4,157,384 | 6/1979 | Watson et al. | 424/45 |
| 4,170,632 | 10/1979 | Wagenknecht et al. | 424/48 |
| 4,550,018 | 10/1985 | Ambike et al. | 424/52 |
| 4,664,906 | 5/1987 | Sipos et al. | 424/49 |
| 4,689,214 | 8/1987 | Niles et al. | 424/49 |
| 4,945,087 | 7/1990 | Talwar et al. | 514/60 |
| 4,992,259 | 2/1991 | Schiraldi et al. | 424/49 |
| 5,002,970 | 3/1991 | Eby, III | 514/494 |
| 5,095,035 | 3/1992 | Eby, III | 514/494 |
| 5,174,990 | 12/1992 | Douglas | 424/53 |
| 5,587,147 | 12/1996 | Domke et al. | 424/54 |
| 5,723,106 | 3/1998 | Buch et al. | 424/49 |
| 5,843,466 | 12/1998 | Mane et al. | 424/401 |

FOREIGN PATENT DOCUMENTS

| | | |
|---|---|---|
| 0251542 | 1/1988 | European Pat. Off. . |
| 9304664 | 3/1993 | WIPO . |
| 9407477 | 4/1994 | WIPO . |
| 9707771 | 3/1997 | WIPO . |

OTHER PUBLICATIONS

Clinic Pak about "Breath Rx" from Discus Dental Oral Hygiene, Los Angeles, California, date unknown.

Pader, M, Oral Hygiene Products and Practice, pp. 344–358, 1988.

Verran, J, Dental plaque—associated infections and antibacterial oral hygiene products, Int. J. Cosmet. Sci., vol. 13, pp. 29–42, 1991.

Cummins, D, Zinc citrate/Triclosan: a new anti–plaque system for the control of plaque and the prevention of gingivitis: short–term clinical and mode of action studies, J. Clin. Periodontal, vol. 18, pp. 455–461, 1991.

Marsh, PD, Dentifrices containing new agents for the control of plaque and gingivitis: microbiological aspects, J. Clin. Periodontal, vol. 18, pp. 462–467, 1991.

Harrap, GJ, Saxton, CA, Best, JS, Human oral retention of zinc from mouthwashes containing zinc salts and its relevance to dental plaque control, Archs. Oral. Biol., vol. 29 No. 2, pp. 87–91, 1984.

Harrap, GJ, Saxton, CA, Best, JS, Inhibition of plaque growth by zinc salts, Periodontal Res., vol. 18, pp. 634–642, 1983.

Ingram, GS, Edgar, WM, Interactions of Fluoride and Non–fluoride Agents with the Caries Process, Adv. Dent. Res., vol. 18, No. 2, pp. 158–165; 1994.

Ingram, GS, Horay, CP, Stead, WJ, Interaction of Zinc with Dental Mineral, Caries Res., vol. 26, pp. 248–253, 1992.

Gilbert, RJ, Ingram, GS, The Oral Disposition of Zinc Following the Use of an Anticalculus Toothpaste Containing 0.5% Zinc Citrate, J. Pharm. Pharmacol., vol. 40, pp. 399–402, 1988.

*Primary Examiner*—Theodore J. Criares
*Assistant Examiner*—Jennifer Kim
*Attorney, Agent, or Firm*—Evan J. Federman

[57] ABSTRACT

Oral compositions including zinc and a coolant provide extended breath freshening without the poor taste and astringency associated with zinc containing compositions.

5 Claims, No Drawings

ORAL COMPOSITIONS CONTAINING A ZINC COMPOUND

This application claims the benefit date of Provisional application Ser. No. 60/027,435 filed Sep. 20, 1996.

FIELD OF THE INVENTION

The invention relates generally to oral compositions containing a Zinc compound together with selected essential oils, as well as oral compositions containing Zinc compounds and a coolant. Such oral compositions are liquids, pastes and gels for the prevention and elimination of bad breath as well as for the reduction of oral microorganisms responsible for the development of dental plaque, gingivitis and tooth decay. A preferred embodiment of the present invention relates to a mouthwash containing zinc chloride, essential oils, and a specific coolant.

1. Description of the Related Art

Oral compositions, such as mouthwashes, have been used by people for many years for the prevention of bad breath and for the elimination of bacteria and other oral microorganisms that are responsible not only for bad breath but also tooth decay, plaque and gum diseases such as gingivitis and periodontitis. Antiseptic mouthwashes in the past have been designed to clean the oral cavity, provide fresh breath and kill these pathogenic microbes.

Thymol is a well known antiseptic agent, also known as an essential oil, which is utilized for its antimicrobial activity in a variety of mouthwash preparations. In particular, thymol can be utilized in oral hygiene compositions such as mouth rinses in sufficient quantities to provide desired beneficial therapeutic effects. LISTERINE®-brand mouthwash is a well-known antiseptic mouthwash that has been used by millions of people for over one hundred years and has been proven effective in killing microbes in the oral cavity that are responsible for plaque, gingivitis and bad breath. Thymol, together with other essential oils such as methyl salicylate, menthol and eucalyptol, are active ingredients (e.g., antimicrobial agents) in antiseptic mouth rinses such as LISTERINE®. These oils achieve their efficacy although present in small amounts. Without being restricted to any specific theory, it is now believed that the efficacy and taste of antiseptic mouthwashes such as Listerine® may be due to the dissolution and delivery kinetics of these four active ingredients.

Zinc salts have been used over the years in several oral care products, primarily to limit or prevent malodor. Examples of such oral care products include AIM® toothpaste, Breath Savers® mints, Lavoris® mouthwash, Viadent® mouthrinse, and Listermint®.

The literature in this field shows there are numerous reasons to add zinc salts to oral care products. Among those reasons are its efficacy as an anti-malodor agent. Two mechanisms of action are believed to be responsible for zinc's utility as an anti-malodor agent. The first is its ability to form insoluble salts with nucleophilic compounds such as valeric acid, hydrogen sulfide, mercaptans, etc., (i.e. volatile sulfur compounds, "VSCs") which typically cause oral malodor. U.S. Pat. No. 4,992,259; Pader, M, Oral Hygiene Products and Practice, Chapter 10, pg. 351. Additionally, the literature shows that zinc salts inhibit proteolysis by direct action on bacterial proteases, like cysteine and methionine proteases, thus reducing the amount of odor causing agents. Marsh, P D, J. Clin. Periodontal, 18(6): 462–467, 1991.

Zinc has also been shown to have antimicrobial efficacy. Here, its mode of action is believed to result from surfactant charge activity, resulting in disruption of membranes. Verran, J. Int. J. Cosmet. Sci., 13: 29–42, 1991, as well as inhibition of essential enzymes in glucose transport and catabolism. Cummins D. J. Clin. Periodontol, 18: 455–461, 1991; and Marsh, P D, J. Clin. Periodontal, 18(6); 462–467, 1991.

Antiplaque and antigingivitis efficacy is another attribute of zinc salts. Part of this activity may be a direct consequence of its antimicrobial efficacy. Further, zinc may reduce the rate of bacterial adherence to teeth. Harrap, G J, Saxton, C A, Best, J S, Archs.Oral. Bio., 29(2): 87–91, 1984; and Harrap, G J, Saxton, C A, Best, J S, J. Periodont Res., 18: 634–642, 1983. Zinc is also said to prevent the toxic effects that volatile sulfur compounds have on membrane permeability by preventing VSC penetration into epithelial cells. Pader, M, Oral Hygiene Products and Practice, Chapter 10, pg. 351–352.

Moreover, zinc has been associated with anticaries activity resulting from inhibition of the dissolutive process of caries by reversible adsorption on apatite. Ingram, G S, Edgar, W M, Adv. Dent. Res., 8(2): 158–65, 1994.

Finally, zinc salts are believed to also have anticalculus efficacy resulting from adsorption of zinc ion on apatite, thus restricting crystal growth. Ingram, G S, Edgar, W M, Adv. Dent. Res., 8(2): 158–65, 1994; Ingram, G S, Horay, C P, Stead, W J, Caries, Res., 26(4): 248–253, 1992 and Gilbert, R J, Ingram, G S, J. Pharm. Pharmacol., 40(6): 399–402, 1988.

Use of zinc salts in oral compositions has several drawbacks, however. An unpleasant aftertaste frequently occurs, which is often characterized as metallic or astringent. Such unpleasant aftertaste limits consumer acceptance of oral care products containing zinc.

Many mouthwash compositions have been used over the years, as noted above, and many have been demonstrated to reduce oral odors and kill germs found in the oral cavity, such as Listerine® mouthwash. However, improved efficacy of these products is desired.

An oral composition which leaves breath feeling fresh overnight and which leaves breath fresh in the morning is desired.

Another area of improvement would be to provide a mouthwash with the ability to fight the development of bad breath over a period of hours and provide fresh feeling breath for several hours.

Enhanced antimicrobial activity, and therefore enhanced effect against malodor, plaque and gingivitis is also desired. An improved caries preventing formulation is also desired.

Achievement of these objectives while also maintaining a high degree of consumer acceptance is also desired. For example, an improved oral care product should provide the user with a cooling or freshening sensation in the mouth and no astringent or metallic aftertaste. A slick feeling on the teeth together with a feeling of oral cleanliness is also desirable. A feeling of tingling or invigoration of the gums is desired, as well as a bite/bum sensation associated with the use of Listerine® mouthwash. In addition, there is a need for such oral compositions to kill the oral microflora responsible for oral problems and clean the oral cavity leaving a fresh, lubricous mouth feel.

Achieving these objectives without a metallic or astringent aftertaste is also desired.

SUMMARY OF THE INVENTION

The present invention is an oral composition containing a zinc salt and essential oils; a zinc salt together with a coolant; or a zinc salt, essential oils, and a coolant.

One aspect of this invention is the combination of zinc salts in conjunction with essential oils used in oral compositions. More specifically, this invention includes the combination of zinc salts with thymol together with one or more of eucalyptol, menthol or methyl salicylate.

Another aspect of this invention includes the combination of zinc salts in conjunction with a coolant in an oral care composition.

Yet a further embodiment of the present invention is the combination of a zinc salt with the essential oil thymol together with one or more of eucalyptol, menthol or methyl salicylate and a coolant in an oral composition.

DETAILED DESCRIPTION OF THE INVENTION

The compositions of the present invention prevent oral malodor for several hours, as well as overnight. They are also antiseptically effective against microorganisms, particularly microorganisms that cause oral malodor, the build-up of plaque and calculus, and the resulting tooth and gum diseases that may follow. Further, the oral compositions of the present invention can help inhibit the adherence of bacteria to teeth and also inhibit the dissolutive process of caries formulation. Compositions of this invention are also believed to have anticalculus activity. Additionally, the compositions of this invention provide a cooling and freshening sensation, as well as other oral sensations desired by the consumer, while masking the metallic astringency of zinc.

It is believed that the combination of essential oils and zinc salts in an oral composition would synergistically reduce oral malodor. Oral compositions with both one or more essential oils and zinc salts are expected to reduce oral malodor better than oral compositions with either one or these components alone.

The oral compositions of the present invention are mouthwash or mouthrinse, and dentifrices such as toothpaste, gels, and toothpowders. Mouthwashes are the preferred embodiment.

One embodiment of the present invention is the combination of zinc salts with thymol and/or one or more other essential oils in an oral composition. Preferably, the essential oils are eucalyptol, menthol or methyl salicylate, or mixtures thereof Most preferably, this embodiment contains all four of these essential oils.

Another embodiment of the present invention is the combination of zinc salts with thymol and/or one or more other essential oils, together with a coolant in an oral composition.

Yet another embodiment of this invention is the combination of a zinc salt together with a coolant in an oral composition.

All embodiments of the oral compositions of this invention contain a zinc salt.

Suitable zinc salts are well known in the art, and are those which freely ionize in an aqueous or hydroalcohol base. Suitable salts include inorganic, organic and water insoluble and water soluble zinc salts. Nonlimiting examples of suitable zinc salts that may be employed include:

| | |
|---|---|
| zinc oxide | zinc stearate |
| zinc tribromosalicylanilide | zinc methionine sulfate |

-continued

| | |
|---|---|
| zinc carbonate | zinc tannate |
| zinc caprylate | zinc octoate |
| zinc oleate | zinc laurate |
| zinc silicate | zinc fluoride |
| zinc acetate | zinc formate |
| zinc lactate | zinc succinate |
| zinc fumarate | zinc iodide |
| zinc ammonium sulfate | zinc nitrate |
| zinc bromide | zinc phenol sulfonate |
| zinc chloride | zinc salicylate |
| zinc chromate | zinc sulfate |
| zinc citrate | zinc gluconate |
| zinc dithionate | zinc succinate |
| zinc fluorosilicate | zinc glycerophosphate |
| zinc tartarate | |

Preferred salts are zinc chloride, zinc citrate, zinc oxide, zinc acetate, zinc stearate, zinc methionine sulfate, zinc phenol sulfonate, zinc sulfate, and zinc gluconate. The most preferred salts are zinc chloride, zinc sulfate, and zinc citrate.

The amount of zinc ion used in any of the embodiments of this invention may vary with the overall composition. However, oral compositions containing up to 5% w/v of zinc ion are useful in the present invention. A preferred range is up to about 2.5% w/v of zinc ion. Most preferred range is 0.015–1.5% w/v of zinc ion.

Also useful in embodiments of our invention is a coolant which is sold by Mane U.S.A., Wayne, N.J. This compound provides a cooling and refreshing sensation and also masks the metallic aftertaste resulting from including zinc in the oral composition.

The amount of the coolant used in a composition will vary with the overall composition and the flavor selected for the composition. Selection of an appropriate amount is believed to be within the ordinary skill in the art. The amount of coolant should be sufficient to reduce or eliminate the metallic/astringent taste of zinc. However, amounts of the coolant ranging from about 0.001 to about 0.4% are suitable. Using about 0.005% to about 0.1% of the coolant is preferred, with about 0.01% to about 0.050% being the most preferred range.

The coolant of this invention is selected from monomenthyl succinate, alkali metal salts of monomenthyl succinate and alkaline earth metal salts of monomenthyl succinate (hereinafter collectively referred to as "coolants" or "succinate based coolant compounds".)

In a second aspect, the present invention relates to a composition including a coolant selected from monomenthyl succinate, alkali metal salts of monomenthyl succinate and alkaline earth metal salts of monomenthyl succinate formulated with a diluent selected from the group of flavors, sweetening syrups, flavoring oils, and herbal oils.

The present invention also relates to coolant compositions which include a primary coolant selected from monomenthyl succinate, alkali metal salts of monomenthyl succinate and alkaline earth metal salts of monomenthyl succinate, and at least one secondary coolant component.

Monomenthyl succinate is a known compound having Chemical Abstracts No. 77341-67-4. It has been used, for example, in smoking tobacco as is disclosed in U.S. Pat. No. 3,111,127. In particular, this patent discloses smoking tobacco which incorporates a monoester of synthetic or natural menthol and a saturated or unsaturated aliphatic or aromatic polycarboxylic acid or a substituted analog of such an acid. These tobacco products were evaluated and observed to burn slower and smolder than a comparable control product, to have increased firmness, and to require more puffs under a controlled smoking regime. Further, when tested organoleptically, these products were found to deliver smoke having the pleasing and cooling taste and aroma characteristic of menthol. Among the polycarboxylic acid esters are mentioned methylsuccinic acid ester, mono menthylsuccinate, monomenthyl-α-α-dimethylsuccinate and mono menthol-menthylsuccinate.

The article, "A Molecular Approach to Flavor Synthesis. I. Menthol Esters of Varying Size and Polarity," Jabloner, H. and Dunbar, B. I., *J. of Polymer Science*, Vol. 18, pages 2933–40 (1980) discloses a method for the synthesis of monomenthyl succinate as well as monomenthyl sodium succinate and other menthol esters derived from monomenthyl succinate. Solutions of 5% by weight of several of these menthol esters in mineral oil or water were tasted by a nine-person taste panel: 5% of dimenthyl succinate in mineral oil was found to be odorless and tasteless; 5% sodium monomenthyl succinate in water was found to be vile and bitter; and monomenthyl succinate itself was not tasted.

It has been surprisingly found that monomenthyl succinate, alkali metal salts of monomenthyl succinate and alkaline earth metal salts of monomenthyl succinate used in a variety of ingestible and topical products at low concentrations of up to 1% by weight, give a pleasing, long-lasting cooling effect rather than the vile and bitter taste observed by the taste panel in the Jabloner article.

More preferably, the coolant employed in the compositions of the present invention is selected from monomenthyl succinate, monomenthyl sodium succinate, monomenthyl potassium succinate, mono menthyl lithium succinate, monomenthyl calcium succinate, monomenthyl magnesium succinate and monomenthyl barium succinate, as well as mixtures thereof.

It has been surprisingly found that these succinate-based coolant compounds, when used in low concentrations of up to 1% by weight based on the total weight of the end use composition into which they are incorporated, provide a pleasing and/or long-lasting cooling effect without the bitterness which would be expected from the prior art. Further, at concentrations of up to 1% by weight, the succinate-based coolant compounds do not develop a strong minty taste in the mouth or throat as do other coolants such as menthol.

The succinate-based coolant compounds of the present invention also provide a cooling effect in a different area of the mouth and throat when ingested than, for example, menthol or carboxamide-based coolant compounds. As a result, the succinate-based coolants of the present invention provide a complementary or synergistic cooling effect when combined with at least one secondary coolant compound.

Further, the succinate-based coolant compounds of the present invention enhance the taste sensation of alcohol in alcoholic beverages. As a result, alcoholic beverages comprising the succinate-based coolant compounds of the present invention taste like they have a higher alcohol content than equally strong alcoholic beverages without the succinate-based coolant compound.

The choice of the succinate-based coolant compound for use in the coolant composition will depend, to some extent, on the solubility characteristics which are desired of the compound. For example, monomenthyl succinate is sparingly soluble in water and more soluble in oil. Thus, monomenthyl succinate is particularly suitable for environments where oil solubility is advantageous, although monomenthyl succinate can be used in aqueous environments if a concentration below the water solubility limit is employed. The alkali metal and alkaline earth metal salts of monomenthyl succinate are substantially more soluble in water and, as a result, are most useful in products where water solubility is advantageous.

In formulating the compositions of the present invention, the coolant compound can be employed in the form of a coolant composition, a flavoring composition and/or the coolant compound, composition or flavoring composition may be incorporated into a carrier material which may be inert or may contain other active ingredients of the end use composition. A wide variety of carrier materials can be employed including, for example, polar solvents, oils, fats, finely divided solids, maltodextrins, cyclodextrins, gums, natural or synthetic resins and any other known carrier materials for coolant or flavoring compositions.

The amount of coolant composition incorporated in each of these end use compositions will vary depending upon the particular compound, the degree of cooling effect desired and the strength of other flavorants in the composition. Typically, the succinate-based coolant compound will make up from 0.001–1.0% by weight of the end use composition. More preferably, the succinate-based coolant compound makes up 0.005–0.5% by weight, based on the total weight of the end use composition.

In a second aspect, the present invention relates to a flavoring composition including a succinate-based coolant and a diluent selected from flavorants. This composition is particularly useful as a flavoring composition in a variety of ingestible compositions and/or compositions destined for contact with the human or animal body.

The flavorants may be selected from fruit flavors such as strawberry flavor, herbal oils such as eucalyptus oil, peppermint oil, spearmint oil, as well as other known flavors or flavoring oils which are conventionally employed in ingestible compositions and compositions designed for contact with human or animal bodies including flavors such as flavoring syrups such as sorbitol syrup or other sweetening or flavoring syrups.

These flavoring compositions can be optionally diluted with a polar solvent such as, for example, ethyl alcohol, ethyl acetate, propylene glycol, isopropyl alcohol, and glycerin. The solvent functions as a carrier material which aids in incorporating the flavoring composition into the product. The diluent may optionally comprise one or more additional conventional components selected from the group consisting of colorants, lubricants, thickeners, emulsifiers, plasticizers, and encapsulating agents such as gums, starches, dextrins, and cyclodextrins.

Typically the flavoring composition will include 1–80% by weight of the succinate-based coolant compound and from 20–99% by weight of the flavorant diluent and optional polar solvent. More preferred flavorant compositions comprise 5–50% by weight of the succinate-based coolant compound and 50–95% by weight of the flavorant diluent and optional polar solvent.

In this invention, the coolant in the Examples includes 98% by weight monomenthyl succinate and 2% by weight flavorant diluent and is available from Mane USA, Wayne, N.J.

The present invention also relates to a combination of a primary cooling agent selected from monomenthyl succinate, alkali metal salts of monomenthyl succinate, alkaline earth metal salts of monomenthyl succinate and mixtures thereof, with at least one secondary coolant component.

Secondary coolant components which may be used in combination with the primary coolant of the present invention include menthol, carboxamides, ketals, menthyl acetate, menthyl lactate, 3-menthoxypropane-1,2 diol and mixtures thereof. The carboxamide and ketal coolant compositions are known from the prior art and can be found, for example, in U.S. Pat. No. 5,009,893 and international patent application publication No. WO-93/23005, the entire disclosures of which are hereby incorporated by reference. The remaining secondary coolants are known cooling agents, some of which are commercially available.

More particularly, the carboxamide secondary coolants are selected from N-substituted-p-menthane-3-carboxamides of the formula:

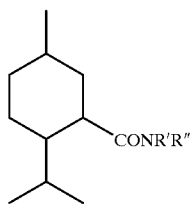

wherein R', when taken separately, is hydrogen or an aliphatic radical containing up to 25 carbon atoms; R" when taken separately is hydroxy or an aliphatic radical containing up to 25 carbon atoms, with the proviso that when R' is hydrogen, R" may also be an aryl radical of up to 10 carbon atoms and selected from the group consisting of substituted phenyl, phenylalkyl, substituted phenylalkyl, naphthyl, substituted naphthyl and pyridyl; and R' and R", when taken together with the nitrogen atom to which they are attached, represent a cyclic or heterocyclic group of up to 25 carbon atoms; acyclic tertiary and secondary carboxamides of the formula:

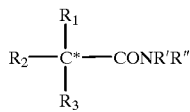

where R' and R", when taken separately, are each hydrogen $C_1$–$C_5$ alkyl or $C_1$–$C_8$ hydroxylalkyl and provide a total of no more than 8 carbon atoms, with the proviso that when R' is hydrogen R" my also be alkylcarboxyalkyl of up to 6 carbon atoms; R' and R", when taken together, represent an alkylene group of up to 6 carbon atoms, the opposite ends of which group are attached to the amide nitrogen atom thereby to form a nitrogen heterocycle, the carbon chain of which may optionally be interrupted by oxygen; $R_1$ is hydrogen or $C_1$–$C_5$ alkyl; and $R_2$ and $R_3$ are each $C_1$–$C_5$ alkyl; with the provisos that (i) $R_1$, $R_2$, and $R_3$ together provide a total of at least 5 carbon atoms, preferably from 5–10 carbon atoms; and (ii) when $R_1$ is hydrogen, $R_2$ is $C_2$–$C_5$ alkyl and $R_3$ is $C_2$–$C_5$ alkyl and at least one of $R_2$ and $R_3$ is branched, preferably in an alpha or beta position relative to the carbon atom marked (*) in the formula; and mixtures thereof.

The ketal coolant compositions may be represented by the formula:

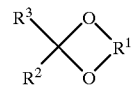

in which $R^1$ represents a $C_2$–$C_6$-alkylene radical having at least 1, but not more than 3, hydroxyl group(s) and either $R^2$ and $R^3$ independently of one another represent $C_1$–$C_{10}$-alkyl which is optionally substituted by 1 to 3 radicals selected from the group comprising hydroxyl, amino, and halogen, $C_5$–$C_7$-cycloalkyl, preferably cyclohexyl, and $C_6$–$C_{12}$-aryl, preferably phenyl, with the proviso that the total of the C atoms of $R^2$ and $R^3$ is not less than 3, or $R^2$ and $R^3$ together represent an alkylene radical which, together with the carbon atom which carries the radicals $R^2$ and $R^3$, forms a 5–7 membered ring, optionally substituted by $C_1$–$C_6$-alkyl groups.

The relative amounts of the primary and secondary coolants in the composition of the present invention may be varied over a wide range of compositions depending upon the particular flavor desired. For example, when the strong minty taste of menthol is desirable, a combination of a large quantity of menthol with a relatively small quantity of the succinate-based coolant of the present invention may be desirable. Other potential combinations of the primary coolant with one or more secondary coolant components will be apparent to the man of skill in the art.

Generally, the level of the secondary coolant component in the coolant composition of the present invention is from about 0.05% by weight to about 95% by weight, more preferably from about 0.1% by weight to about 70% by weight, and most preferably from about 0.5% by weight to about 50% by weight, based on the total weight of the composition. Typically, the coolant compositions are made by mixing the primary and secondary coolants together in a conventional manner.

Thymol, $(CH_3)_2CHC_6H_3(CH_3)OH$ (isopropyl-m-cresol), is only slightly soluble in water but is soluble in alcohol. Methyl salicylate, $(C_6H_4OHCOOCH_3)$, also known as wintergreen oil, additionally provides flavoring to the mouthwash together with an antimicrobial function. Eucalyptol $(C_{10}H_{18}O$; cineol) is a terpene ether and provides a cooling, spicy taste. Menthol $(CH_3C_6H_9(C_3H_7)OH$; hexahydrothymol) also is highly soluble in alcohol, is fairly volatile, and in addition to any antiseptic properties provides a cooling, tingling sensation.

In the oral compositions of this invention, the essential oils are used in amounts effective to provide antimicrobial activity in the oral cavity. Generally, the total amount of essential oils present in a mouthwash or mouthrinse composition of this invention can be from about 0.001% to about 0.35% w/v, with about 0.16% to about 0.28% w/v being preferred. Amounts employed in dentifrice will generally be greater and can be readily ascertained by those skilled in the art. Generally the total amount of essential oils will be from 0.01% to about 3.5% w/v, preferably from about 0.008% to about 2.80% w/v.

Thymol is preferably employed in the mouthwash composition of this invention in amounts of from about 0.001% to about 0.35% w/v, and most preferably from about 0.04% to about 0.07% w/v. Eucalyptol is preferably employed in amounts of from about 0.001% to about 0.20% w/v, and most preferably from about 0.085% to about 0.10% w/v. Menthol is preferably employed in amounts of from about 0.001% to about 0.35% w/v and most preferably from about 0.035 to about 0.05% w/v. Methyl salicylate is preferably employed in amounts of from about 0.001% to about 0.30% w/v, and most preferably from about 0.04% to about 0.07% w/v.

The mouthwash compositions of this invention, containing a zinc salt and thymol and at least one other essential oil provide effective antimicrobial activity without the presence of other types of antimicrobial agents. However, the oral compositions of the present invention may contain numerous other well known ingredients, including additional antimicrobial agents. Exemplary antimicrobial agents which may be employed include, without limitation, essential oils, cetyl pyridium chloride (CPC), chlorhexidine, triclosan, hydrogen peroxide, domiphen bromide and the like.

The vehicle for the antimicrobial compositions of this invention, and particularly for the compositions containing essential oils may be an aqueous medium. The aqueous medium may be a water-alcohol mixture, generally a water-ethanol mixture. Alternatively, in the case of ethanol-free compositions, the aqueous medium is water. In the past, most antiseptic oral mouthwash compositions, such as LISTERINE®-brand mouthwashes, required high ethanol levels of up to about 27% v/v. These high levels of ethanol were necessary for the antimicrobial agents to be acceptably effective as well as to provide a clear, aesthetically attractive liquid medium.

In a preferred embodiment of this invention, the oral composition contains a $C_3$–$C_6$ alcohol in conjunction with ethanol, thus reducing the quantity of ethanol in the composition. Examples of suitable alcohols include, but are not limited to 1-propanol, 2-propanol, 1-butanol and tert-butanol. A more complete discussion of the use of $C_3$–$C_6$ alcohols in oral care compositions may be found in copending U.S. patent application Ser. No. 08/540,861 filed Oct. 11, 1995, which is hereby incorporated by reference in its entirety.

Surface active agents (surfactants) may be employed in the compositions of the present invention. They are organic materials which aid in the complete dispersion of the ingredients throughout the solution as well as dispersing the preparation throughout the oral cavity. Preferably, the surfactant used in the compositions of the present invention is a non-ionic surfactant, anionic surfactant, or cationic surfactant employed in an amount sufficient to help solubilize the actives. By sufficient amount it is meant that the surfactant is present in an amount that effectively assists in the solubilization and delivery system kinetics of the essential oils.

The preferred non-ionic surfactants are selected from the group known as poly(oxyethylene)-poly(oxypropylene) block copolymers. Such copolymers are known commercially as poloxamers and are produced in a wide range of structures and molecular weights with varying contents of ethylene oxide. These non-ionic poloxamers are non-toxic and acceptable as direct food additives. They are stable and readily dispersible in aqueous systems and are compatible with a wide variety of formulations and other ingredients for oral preparations. These surfactants should have an HLB (Hydrophilic-Lipophilic Balance) of between about 10 and about 30 and preferably between about 10 and about 25.

By way of example, non-ionic surfactants useful in this invention include the following poloxamers:

| 105 | 188 | 237 | 334 |
| 108 | 215 | 238 | 335 |
| 124 | 217 | 284 | 338 |
| 184 | 234 | 288 | 407 |
| 185 | 235 | 333 | |

Generally these polymers when used are present in amounts of from about 0.01% w/v to about 8.0% w/v, and preferably from about 0.10% to about 0.75% w/v. A particularly preferred poloxamer is poloxamer 407 which is incorporated in an amount of about 0.1 to 4.5% w/v.

The cationic surfactants are generally selected from amines, such as aliphatic mono, di, and polyamines derived from fatty and rosin acids, as well as amine oxides, ethonxylated alkylamines, 1-(2-hydroxyethyl)-2-imidazolines and alkoxylates of ethylenediamine, quaterary ammonium salts such as dialkyldimethylammonium salts, poloxamines (tetra-functional block copolymer), alkylbenzyldimethylammonium chlorides, alkyltrimethylammonium salts, alkylpyridinium halides and the like. Preferred exemplary cationic surfactants include, without limitation, cetyl pyridinium chloride, benzethonian chloride, chlorhexidine, domiphen bromide, benzalkonium chloride, dequalinium chloride and the like. Cetyl pyridinium chloride is most preferred.

The preferred anionic surfactants are selected from sodium lauryl sulfate, magnesium lauryl sulfate, Tauranol® and the like. Tauranol® is sodium-N-methyl-N-cocoyl taurate available from Finetex, N.J. Generally, the anionic surfactants when used are present in amounts of about 0.001% to about 4.0% w/v, and preferably from about 0.005% about 2.0% w/v.

The surfactant is used to help solubilize the essential oils and flavor oils which may otherwise not be soluble in these aqueous systems due to the level of ethanol. The surfactant (s) also act to disperse the actives and flavors throughout the solution and enable the compositions to provide a clear, uniform appearance that is aesthetically more appealing.

The essential oil methyl salicylate not only provides antimicrobial activity but, being a wintergreen flavor oil, also adds to the organoleptic flavor.

The particular flavor oils and other taste-enhancing ingredients employed will vary depending upon the particular taste and feel desired. Those skilled in the art can select and customize these types of ingredients to provide the desired results.

The flavorings (flavoring agents) that may be used include those known to the skilled artisan, such as natural and artificial flavors. These flavorings may be chosen from synthetic flavor oils and flavoring aromatics, and/or oils, oleo resins and extracts derived from plants, leaves, flowers, fruits and so forth, and combinations thereof. Representative flavor oils include- spearmint oil, cinnamon oil, oil of wintergreen (methyl salicylate), peppermint oil, clove oil, bay oil, eucalyptus oil, thyme oil, cedar leaf oil, oil of nutmeg, oil of sage, and oil of bitter almonds. Also useful are artificial, natural or synthetic fruit flavors such as vanilla, and citrus oil, including lemon, orange, grape, lime and grapefruit and fruit essences including apple, pear, peach, strawberry, raspberry, cherry, plum, pineapple, apricot and so forth. These flavorings may be used individually or in admixture. Commonly used flavors include mints such as peppermint, menthol, artificial vanilla, cinnamon derivatives, and various fruit flavors, whether employed individually or in admixture.

Flavorings such as aldehydes and esters including cinnamyl acetate, cinnamaldehyde, citral, diethylacetal, dihydrocarvyl acetate, eugenyl formate, p-methylanisole, and so forth may also be used. Generally any flavoring or food additive such as those described in *Chemicals Used in Food Processing*, pub. 1274 by the National Academy of Sciences, pages 63–258 may be used.

Further examples of aldehyde flavorings include, but are not limited to acetaldehyde (apple); benzaldehyde (cherry, almond); cinnamic aldehyde (cinnamon); citral, i.e., alpha citral (lemon, lime); neral, i.e. beta citral (vanilla, cream); heliotropine, i.e. piperonal (vanilla, cream); vanilla (vanilla, cream); alpha-amyl cinnamaldehyde (spicy fruity flavors); butyraldehyde (butter, cheese); valeraldehye (butter, cheese); citronella (modifiers, many types); decanal (citrus fruits); aldehyde C-8 (citrus fruits); aldehyde C-9 (citrus fruits); aldehyde C-12 (citrus fruits); 2-ethyl butyraldehyde (berry fruits); hexenal, i.e. trans-2 (berry fruits); tolyl aldehyde (cherry, almond); veratraldehyde (vanilla); 2,6-dimethyl-5-heptenal, i.e. melonal (melon); 2-6-dimethyloctanal (green fruit); and 2-dodecenal (citrus, mandarin); cherry; grape; mixtures thereof; and the like.

Various other physiological cooling agents may be used in the composition of this invention. Cooling agents suitable for use herein include carboxamides, methane esters and methane ethers, and mixtures thereof. Examples of cooling agents within each of these categories, suitable for use in such a composition, include but are not limited to, WS3® (N-ethyl-p-methane-3-carboxamide) discovered by Wilkinson Sword, marketed by Sterling Organics (now ChiRex), Optacool® (menthyl lactate) from Haarmann & Reimer Corp, and MPD® (3-1-menthoxy propan-1,2-diol) from Takasago International Corp. respectively.

The amount of additional physiological cooling agent used would depend on the intensity of cooling desired by consumers. In the present invention an accepted level would be up to 0.25% w/v of the cooling compound with a preferred range of 0.001% to about 0.05%.

The amount of flavoring employed is normally a matter of preference subject to such factors as flavor type, individual flavor, and strength desired. Thus, the amount may be varied in order to obtain the result desired in the final product. Such variations are within the capabilities of those skilled in the art without the need for undue experimentation. In general, amounts of about 0.005% to about 2.0% by weight of the composition are usable with amounts of about 0.05% to about 1.5% being preferred.

The compositions of this invention may also contain coloring agents or colorants.

The coloring agents are used in amounts effective to produce the desired color. The coloring agents (colorants) useful in the present invention include natural foods colors and dyes suitable for food, drug and cosmetic applications. These colorants are known as F.D. & C. dyes and lakes. The materials acceptable for the foregoing spectrum of use are preferably water-soluble, and include indigiod dye, known as F.D. & C. Blue No. 2, which is the disodium salt of 5,5-indigotindisulfonic acid. Similarly, the dye known as Green No. 1 comprises a triphenylmethane dye and is the monosodium salt of 4-[4-N-ethyl-p-sulfobenzylamino) iphenylmethylene]-[1-N-ethyl-N-p-sulfoniumbenzyl)-$D^{2,5}$-cyclohexadienimine]. Additional examples include the yellow dye, known as D&C Yellow No. 10, and the dye known as F.D. & C. Green No. 3 which comprises a triphenylmethane dye. A full recitation of all F.D. & C. and D. & C. dyes and their corresponding chemical structures may be found in the Kirk-Othmer Encyclopedia of Chemical Technology, Volume 5, pages 857–884, which text is accordingly incorporated herein by reference.

Fluoride providing compounds may be present in the oral preparations of this invention. These compounds may be slightly water soluble or may be fully water soluble and are characterized by their ability to release fluoride ions or fluoride containing ions in water. Typical fluoride providing compounds are inorganic fluoride salts such as soluble alkali metal, alkaline earth metal, and heavy metal salts, for example, sodium fluoride, potassium fluoride, ammonium fluoride, cuprous fluoride, zinc fluoride, stannic fluoride, stannous fluoride, barium fluoride, sodium fluorozirconate, sodium monofluorophosphate, aluminum mono- and difluorophosphate, fluorinated sodium calcium pyrophosphate, and acidulated monofluorophosphate.

Alkali metal, tin fluoride and monofluorophosphates such as sodium and stannous fluoride, sodium monofluorophosphate and mixtures thereof are preferred.

In an oral liquid preparation such as a mouthwash, the fluoride providing compound is generally present in an amount sufficient to release up to about 0.15%, preferably about 0.001% to about 0.1% and most preferably from about 0.001% to about 0.05% fluoride by weight of the preparation.

If desired, auxiliary sweeteners may be utilized in the compositions of this invention. Those sweeteners which may be included are those well known in the art, including both natural and artificial sweeteners.

The sweetening agent (sweetener) used may be selected from a wide range of materials including water-soluble sweetening agents, water-soluble artificial sweeteners, water-soluble sweetening agents derived from naturally occurring water-soluble sweeteners, dipeptide based sweeteners, and protein based sweeteners, including mixtures thereof. Without being limited to particular sweeteners, representative illustrations encompass:

A. Water-soluble sweetening agents such as monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, and glycyhrrizine;

B. Water-soluble artificial sweeteners such as the soluble saccharin salts, i.e. sodium or calcium saccharin salts, cyclamate salts, the sodium, ammonium or calcium salt of 3,4-dihydro-6-methyl-1,2,3-oxathiazine-4-one-2,2-dioxide, the potassium salt of 3-4-dihydro-6-methyl-1-2,3-oxathiazine-4-one-2,2-dioxide (acesulfame-K), the free acid form of saccharin, and the like;

C. Dipeptide based sweeteners, such as L-aspartic acid derived sweeteners, such as L-aspartyl-L-phenylalanine methyl ester (aspartame) and materials described in U.S. Pat. No. 3,492,131; L-a-aspartyl-N-(2,2,4,4-tetramethyl-3-thietanyl)-D-alaninamide hydrate, methyl esters of L-aspartyl-L-phenylglycerine and L-aspartyl-L-2,5, dihydrophenyl-glycine. L-aspartyl-2,5-dihydro-L-phenylalanine, L-aspartyl-L-(1-cyclohexyen)-alanine; and the like;

D. Water-soluble sweeteners derived from naturally occurring water-soluble sweeteners, such as chlorinated derivatives of ordinary sugar (sucrose), known, for example, under the product description of sucralose; and E. Protein based sweeteners such as thaumatoccous danielli (Thaumatin I and II).

In general, an effective amount of auxiliary sweetener is utilized to provide the level of sweetness desired for a particular composition, and this amount will vary with the sweetener selected. This amount will normally be 0.01% to about 40% by weight of the composition when using an easily extractable sweetener. The water-soluble sweeteners described in category A, above, are usually used in amounts of about 5% to about 40% by weight, and preferably in amounts of about 10% to about 20% by weight of the final composition. Some of the sweeteners in category A (e.g., glycyrrhizin) may be used in amounts set forth for categories B–E below due to the sweeteners' known sweetening ability. In contrast, the sweeteners described in categories B–E are generally used in amount of about 0.005% to about 5.0% by weight of the final composition with about 0.005% to about 2.5% by weight being usual and about 0.001% to about 0.4% by weight being preferred. These amounts may be used to achieve a desired level of sweetness independent from the flavor level achieved from any optional flavor oils used.

Additional conventional components may be added as in mouthwashes of the prior art. Whereas some ethanol containing mouthwashes have a pH of about 7.0, reduction of the ethanol level in the preferred embodiments utilizing $C_3$–$C_6$ alcohols requires the addition of acidic preservatives, such as sorbic or benzoic acid, which reduce pH levels. Buffer systems are then necessary to control the pH of the composition at optimal levels. This is generally accomplished through the addition of a weak acid and its salt or a weak base and its salt. Useful systems have been found to be sodium benzoate and benzoic acid in amounts of from about 0.01% to about 4.0% w/v, and sodium citrate and citric acid in amounts of from about 0.001% to about 0.2% w/v. Preferably the buffers are incorporated in amounts that maintain the pH at levels of from about 3.5 to about 6.5, and more preferably from about 4.0 to 5.0. Without being bound to any theory, it is believed that these pH levels provide the essential oils with an environment that also maximizes their antimicrobial activity.

Other conventional ingredients may be used in the mouthwash compositions of this invention, including those known and used in the art. This includes but is not limited to polyethylene glycol, glycerin, sorbitol, propylene glycol, butylene glycol, xylitol, and mannitol. For example, humectants such as polyethylene glycol may be added as an additional solubilizer for the flavor oils and to also provide texture to the composition. These are incorporated in amounts of from about 0.3% w/v to about 0.20% w/v. For example, a humectant such as glycerin may be added to enhance the lubricous mouthfeel of the mouthwash as it is used and to provide a refreshing, moist, organoleptic feeling thereafter. Glycerin may be incorporated in amounts of from about 0.25% w/v to about 16.0% w/v, and preferably in an amount of about 1.0–2.0% w/v. As another example sorbitol may be incorporated in amounts of from about 1.0% to about 25%, and preferably in an amount of about 10.0% to about 20.0% w/v.

The oral composition of the present invention is preferably a mouthwash but may also be formulated, if desired, as a dentifrice as gels, pastes, or creams using standard dentifrice formulations known in the art as appropriate.

The oral compositions of this invention may also be substantially solid or pasty in character such as a dental cream, toothpaste, or a tooth powder. Solid or pasty oral preparations contain polishing materials. Typical polishing materials are abrasive particulate materials having particle sizes of up to about 20 microns. Nonlimiting illustrative examples include: water-insoluble sodium metaphosphate, potassium metaphosphate, tricalcium phosphate, dihydrated calcium phosphate, calcium pyrophosphate, magnesium orthophosphate, trimagnesium phosphate, calcium carbonate, alumina, aluminum silicate, zirconium silicates, silica, bentonite, and mixtures thereof. Polishing materials are generally present in an amount from about 20% to about 82% by weight of the oral preparation. Preferably, they are present in amounts from about 20% to about 75% in toothpaste, and from about 70% to about 82% in tooth powder. For toothpaste and dental creams the water content is about 25% to 50% by weight.

In clear gels, a polishing agent of colloidal silica and alkali metal aluminosilicate complexes are preferred since they have refractive indicies close to the refractive indicies of gelling agent liquid systems commonly used in dentifrices.

In the oral compositions that are toothpastes, dental creams, or gels the vehicle may comprise water, typically in an amount of about 10–90% by weight of the composition. Polyethylene glycol, propylene glycol, glycerin or mixtures thereof may also be present as humectants or binders in amounts of about 20–25% by weight. Particularly advantageous liquid ingredients comprise mixtures of water with polyethylene glycol or glycerin and propylene glycol. A gelling agent (thickening agent) including natural or synthetic gums such as sodium carboxymethylcellulose, hydroxyethyl cellulose, methyl cellulose and the like may be used, in the range of about 0.5–5% by weight. In a toothpaste, dental cream or gel, the liquids and solids are proportioned to form a creamy or gelled mass which is extrudable from a pressurized container or from a collapsible tube. Topical pastes, creams and gels may also be formulated in a similar manner.

The pastes or gels may also contain a surface active agent which may be an anionic, nonionic or zwitterionic detergent (surfactant) in amounts of about 0.05–5% by weight. The anionic and nonionic surfactants that are suitable have already been discussed above.

Zwitterionic surface active agents include the betaines and sulfobetaines. Typical alkyl dimethyl betaines include decyl betaine or 2-(N-decyl-N,N-dimethylammonio)acetate, coco betaine, cetyl betaine, stearyl betaine, etc. The amidobetaines similarly include cocamidoethyl betaine, cocamidopropyl betaine, lauramidopropyl betaine and the like. These sulfobetaines are similar in structure to the betaines, but have a sulfonate group in place of the carboxylate group, and include alkylsulfobetaines, alkylamidosulfobetaines and alkylaminosulfobetaines.

Water is added to q.s. the composition and the composition may then be bottled and packaged for shipping.

In general, the compositions of this invention are prepared utilizing techniques well known to those skilled in the art. Thus, the liquid compositions may be prepared by mixing the alcohol soluble ingredients with ethanol, adding a quantity of water to the mixture thus obtained, and then blending or mixing in the water soluble ingredients. For example, in preparing one liter of a typical liquid oral composition, thymol, eucalyptol, menthol, methyl salicylate, surfactant, a coolant and benzoic acid are dissolved in and mixed with ethanol. To this resulting mixture a sufficient quantity of water is added, and then the zinc salt, auxiliary sweetener, water soluble colorants, buffers, and the like are blended in. Then additional water is added to make up one liter. In another method, the zinc salt may be added to the ethanol fraction.

Those skilled in the art will appreciate that the total amount of all ingredients (components) used in the compositions of this invention equals 100% by weight of the total composition. Also, unless stated otherwise, all percents herein are percent by weight of the total composition. Certain compositions of the present invention are illustrated by the following examples.

EXAMPLE 1

A mouthwash with the lasting ability to prevent the creation of malodors for several hours was prepared by combining the following components in potable water.

| COMPONENTS | AMOUNT | |
|---|---:|---|
| Ethanol | 216 | mls. |
| Thymol | 0.639 | grams |
| Menthol | 0.425 | grams |
| Methyl Salicylate | 0.66 | grams |
| Eucalyptol | 0.922 | grams |
| $ZnCl_2$ | 1.0 | grams |
| Benzoic Acid | 1.2 | grams |
| Sodium Benzoate | 0.35 | grams |
| Caramel | 0.24 | grams |
| Poloxamer 407 | 2.0 | grams |
| Sorbitol | 200 | grams |
| 1-Propanol (Flavorant) | 5.0 | grams |
| menthyl succinate containing coolant | 0.5 | grams |
| Water | Q.S. to 1 | Liter |

The above composition was prepared by adding the essential oils (thymol, menthol, methyl salicylate and eucalyptol), menthyl succinate coolant, Poloxamer 407, benzoic acid, and 1-propanol to ethanol, followed by the addition of 250 ml of potable water. In this invention the menthyl succinate containing coolant is 98% by weight monomenthyl succinate and 2% by weight flavorant diluent. To that mixture was added $ZnCl_2$, sorbitol, and caramel. Sodium benzoate, zinc chloride, sorbitol, and caramel were then added; q.s. to 1000 ml with purified water.

EXAMPLE 2

A mouthwash containing all the ingredients listed in Example 1 was prepared, however, it did not include menthyl succinate. The method of preparation described in Example 1 was utilized.

EXAMPLE 3

A mouthwash containing all the ingredients listed in Example 1 was prepared, however the menthyl succinate was decreased to 0.04% to decrease the turbidity of the composition.

EXAMPLE 4

COMPARATIVE EXAMPLE

Commercially available Listerine® mouthwash (amber) has the following formula:

| Ingredient | Amount | |
|---|---:|---|
| Ethanol (USP) | 284 | mls |
| Thymol | 0.64 | gram |
| Eucalyptol | 0.92 | gram |
| Menthol | 0.42 | gram |
| Methyl Salicylate | 0.66 | gram |
| Benzoic Acid | 1.5 | grams |
| Caramel | 0.2 | gram |
| Poloxamer 407 | 1.0 | gram |
| Water | Q.S. to 1 | Liter |

The utility of zinc salts and compositions according to the present invention to reduce malodor and inhibit or prevent the development of plaque or gingivitis was demonstrated.

EXAMPLE 5

REDUCTION OF MALODOR

In Vitro Tests

As discussed previously, oral malodor occurs as the result of generation of volatile sulfur compounds (VSC) such as hydrogen sulfide and $CH_3SH$.

To support the development of a superior breath freshening mouthwash, a new in vitro model was developed to assist with the selection of effective VSC reducing ingredients. Currently, the method of choice for measuring oral malodor is a hedonic clinical study in which judges rate clinical samples on a relative scale, via sniffing the level of oral malodor (VSC's) in each subject's breath. This test is expensive, time consuming and subjective, depending upon judges perceptions. Previous studies have used an Interscan® Halimeter available from Interscan Corp., Chatsworth, Calif., to measure VSC's in situ in order to eliminate any personal bias from judges. Unfortunately, these protocols still require the use of human subjects.

The objective of this study was to evaluate the use of pure cultures or oral malodor-causing bacteria as the source of malodor instead of human subjects. Cultures of *Fusobacterium nucleatum, Veillonella parvula* and Prevotella sp. are well recognized producers of VSC's due to their ability to digest amino acids including cysteine and methionine. The most widely investigated of these is *F. nucleatum*. Therefore, this organism was selected for this in vitro test.

Evaluating a finished oral care composition spiked with Fusobacterium was considered, however, the detector in the Halimeter was adversely affected by alcohols. However, it was discovered the solutions of active ingredients alone do not interfere with the Halimeter's sensor. Therefore, the following methodology was applied to screen the effectiveness of various zinc salt solutions in reducing VSC's:

Materials and Methods:

*Fusobacterium nucleatum* (ATCC #10953) was transferred twice from frozen stock cultures and maintained by daily transfers in Schaedlers' broth (Difco or BBL). Overnight cultures were inoculated (10–50 ml) into 3 ml USP water and allowed to react for one minute in a specially designed reaction tube. The tube is a scaled down version of a Kontes #181000 adapter inlet with hose connectors which is coupled to a 18×100 mm glass tube fitted with a tapered ground fitting. After one minute the Halimeter was connected to a port on the reaction tube and allowed to sample the VSC's in the solution via the vacuum pump. The peak reading recorded by the Halimeter was taken as the VSC measurement. The level of inoculum selected was determined by ppb of VSC's generated in inoculated water alone. The inoculum level was adjusted to give a minimum reading of 600 ppb and a maximum reading of 2000 ppb, the Halimeter's upper limit.

Three different zinc salt solutions, $ZnCl_2$, $ZnSO_4$, and ZnO, were evaluated. Each solution was studied at five different concentrations: 0.01, 0.05, 0.1, 0.2 and 0.4%. Water was used as the control. The readings, obtained are reported in the following table. (Table 1) The heading D% refers to the difference between the measurement of VSCs in ppb using a pure water solution and the measurement of VSCs in ppb using varying concentrations of zinc salts. Each experiment was run in triplicate.

As can be seen from the Table 1, zinc salts present in amounts as low as 0.01% significantly reduce the level of VSCs generated by *Fusobacterium nucleatum*, thus evidencing the ability of zinc salts to reduce the creation of oral malodor.

TABLE 1

Effect of Zinc Salts on Generation of Volatile Sulfur from Fusobacterium nucleatum (ATCC 10953)

| Sample | ppb | % D | ppb | % D | ppb | % D |
|---|---|---|---|---|---|---|
| ZnCl$_2$ | | | | | | |
| 0.01 | 606 | −47.4 | 669 | −58.3 | 539 | −37.0 |
| 0.05 | 541 | −53.0 | 681 | −57.5 | 513 | −40.0 |
| 0.1 | 532 | −53.8 | 727 | −54.6 | 487 | −43.1 |
| 0.2 | 463 | −59.8 | 635 | −60.4 | 446 | −47.9 |
| 0.4 | 424 | −63.2 | 659 | −58.9 | 450 | −47.4 |
| ZnSO$_4$ | | | | | | |
| 0.01 | 552 | −52.0 | 517 | −67.7 | 524 | −38.7 |
| 0.05 | 534 | −53.6 | 781 | −51.3 | 492 | −42.5 |
| 0.1 | 521 | −54.7 | 663 | −58.6 | 493 | −42.4 |
| 0.2 | 482 | −58.1 | 523 | −67.4 | 444 | −48.1 |
| 0.4 | 403 | −65.0 | 670 | −58.2 | 419 | −51.0 |
| ZnO | | | | | | |
| 0.01 | 533 | −53.7 | 723 | −54.9 | 513 | −40.0 |
| 0.05 | 591 | −48.7 | 773 | −51.8 | 535 | −37.5 |
| 0.1 | 481 | −58.2 | 680 | −57.6 | 495 | −42.1 |
| 0.2 | 467 | −59.4 | 585 | −63.5 | 446 | −47.9 |
| 0.4 | 458 | −60.2 | 473 | −70.5 | 393 | −54.1 |
| Water | 1290 | | 1674 | | 1087 | |
| | 1124 | | 1532 | | 725 | |
| | 1039 | | [1603] | | 754 | |
| | [1151] | | | | [855.3] | |

EXAMPLE 6

OVERNIGHT EFFICACY

Mouthrinses containing 0.25% zinc (w/v) have also been clinically demonstrated to reduce oral malodor, based on VSC measurements, overnight, to leave breath fresher in the morning.

Materials And Methods

Subjects participating in this study maintained their normal nightly oral hygiene procedure for the duration of the study. In addition, all participants were asked to refrain from eating odoriferous foods at least 24 hours prior to their appointment for measurement of VSC's.

Subjects reported directly to the laboratory each morning for measurement of mouth air VSC levels. This measurement was the baseline (pretreatment) level of VSC. Selection for the study was based on morning levels of H$_2$S above 30 parts per billion (ppb) and CH$_3$SH above 20 ppb. Subjects fulfilling this criteria received a treatment to use that evening. Immediately before retiring to bed, the subjects rinsed vigorously for 30 seconds using the assigned treatment. The following morning the subject returned to the lab for analysis of mouth air VSC. This measurement was the post-treatment value. These treatments were assigned in a random, crossover design experiment. The test rinses consisted of 20 ml of 0.25% zinc chloride USP, (50 mg/dose) and 20 ml of water were prepared, individually sterilized and sealed in glass bottles.

Levels of VSC in subject's mouth air were determined using a gas chromatography system equipped with a flame photometric detector. Results of individual's baseline and post-treatment measurements were analyzed for significance using paired t-tests. Analysis of variance tested for significant treatment differences.

Each subject's baseline (pretreatment) and post-treatment morning mouth air VSC measurements are presented in Tables 2 and 3 as parts per billion (ppb) of H$_2$S and CH$_3$SH. Treatment means and results of the paired t-tests are also presented. The statistical analysis demonstrates that, compared to baseline levels, zinc significantly reduced levels of CH$_3$SH and H$_2$S.

Differences between treatment were tested by analysis of variance using post minus pretreatment levels of mouth air VSCs. This analysis indicated that zinc mouthrinses are superior to water in reducing H$_2$S levels and that the zinc mouthrinse was superior to water in reducing CH$_3$SH.

In summary, a zinc mouthrinse has been shown to be effective overnight in reducing levels of CH$_3$SH and H$_2$S in morning breath.

TABLE 2

Overnight Malodor Study
H$_2$S levels (ppb)

| Subject/ | Water | | Zinc Chloride | |
|---|---|---|---|---|
| Treatment | Baseline | Post | Baseline | Post |
| 1 | 40 | 63 | 344 | 41 |
| 2 | 162 | 262 | 53 | 22 |
| 3 | 190 | 141 | 522 | 162 |
| 4 | 125 | 54 | 204 | 268 |
| 5 | 562 | 194 | 644 | 129 |
| 6 | 50 | 73 | 310 | 106 |
| 7 | 163 | 65 | 91 | 35 |
| 8 | 264 | 193 | 509 | 318 |
| 9 | 59 | 48 | 191 | 32 |
| 10 | 139 | 6 | 175 | 162 |
| 11 | 32 | 187 | 81 | 94 |
| 12 | 34 | 47 | 110 | 17 |
| 13 | 314 | 139 | 170 | 97 |
| x = | 164 | 113 | 262 | 114 |
| Probability (p) t-test for differences from baseline | p = .1879 | | p = .0074* | |
| *Significant reduction from Baseline | | | | |
| Duncan's Multiple Range Test, means with same letter are not significantly different | A | | B | |

TABLE 3

Overnight Malodor Study
CH$_3$SH levels (ppb)

| Subject/ | Water | | Zinc Chloride | |
|---|---|---|---|---|
| Treatment | Baseline | Post | Baseline | Post |
| 1 | 86 | 8 | 173 | 50 |
| 2 | 63 | 160 | 46 | 20 |
| 3 | 112 | 61 | 358 | 63 |
| 4 | 60 | 49 | 115 | 176 |
| 5 | 141 | 66 | 249 | 41 |
| 6 | 38 | 74 | 61 | 35 |
| 7 | 72 | 56 | 51 | 29 |
| 8 | 77 | 52 | 99 | 63 |
| 9 | 26 | 70 | 170 | 25 |
| 10 | 164 | 61 | 217 | 133 |
| 11 | 48 | 90 | 44 | 47 |
| 12 | 47 | 38 | 59 | 16 |
| 13 | 49 | 66 | 34 | 41 |
| x = | 76 | 65 | 129 | 57 |
| Probability (p) t-test for differences from baseline | p = .5095 | | p = .0209* | |
| *Significant reduction from Baseline | | | | |
| Duncan's Multiple Range Test, means with same letter are not significantly different | A | | B | |

EXAMPLE 7

R-FACTOR

Biofilms of the microorganism Streptococcus mutans (ATCC #25175) grown on stainless steel wires simulate thick, semipermeable dental plaque. For purposes of the present invention, an "R-Factor" is a convenient measure of the antimicrobial efficacy of the mouthwash compositions of the present invention, as measured by their ability to kill those biofilms. The R-Factor is defined as the ratio of (1) the time, in minutes, necessary for a mouthwash composition to kill *S. mutans* microorganism biofilms grown in vitro on stainless steel wires, to (2) the time, in minutes, necessary for a standard high ethanol mouthwash composition to kill similar biofilms of the same microorganism grown in vitro on other, identical stainless steel wires. The standard mouthwash composition used is described in Comparative Example 4. Those kill times are obtained by a plaque penetration assay.

The plaque penetration assay is described in detail in copending application Ser. No. 08/540,861 filed Oct. 11, 1995, which has been incorporated by reference in its entirety.

Using this assay, the R-factor for a commercially available mouthwash with 0.2% zinc salt and Sanguinaria was measured, as well as the R-factors for a base formula mouthwash with zinc chloride and zinc gluconate. The base formula mouthwash is the same formula as Example 2. Varying concentrations of zinc salts were added to the base formula and evaluated. The results are tabulated in Table 4.

TABLE 4

Plaque Penetration Results for formulations containing Zinc Salts

Base formulation:

| $ZincCl_2$ (%) | $Zinc^{+2}$ (mM) | R-factor | Average | S.E. | n (# runs) |
|---|---|---|---|---|---|
| 0.00 | 0 | 1.24, 1.40, 1.05, 1.24 | 1.23 | 0.07 | 4 |
| 0.10 | 7.34 | 1.24, 1.40, 0.88, 1.19 | 1.18 | 0.11 | 4 |
| 0.15 | 11.01 | 1.24, 1.40, 1.00, 1.24 | 1.22 | 0.08 | 4 |
| 0.20 | 14.67 | 1.12, 1.13, 0.93, 0.88 | 1.02 | 0.06 | 4 |

Base formulation:

| Zinc gluconate (%) | $Zinc^{+2}$ (mM) | R-factor | Average | S.E. | n (# runs) |
|---|---|---|---|---|---|
| 0.374 | 7.34 | 1.00, 1.40, 1.15, 0,91 1.00 | 1.09 | 0.09 | 5 |

Commercially available mouthwash with 0.2% zinc salt and sanguinaria

| Zinc chloride (%) | $Zinc^{+2}$ (mM) | R-factor | Average | S.E. | n (# runs) |
|---|---|---|---|---|---|
| 0.20 | 14.67 | >2.5 | — | — | 1 |

The high R-factor value (i.e. >2.5) obtained for the commercial mouthrinse, containing 0.20% Zinc chloride, indicates that it takes this product significantly longer than the standard mouthwash formula to kill the biofilms. R-factor values of this magnitude suggest the subject mouthwash will not be effective at preventing or inhibiting the development of plaque or gingivitis in clinical trials.

In contrast, the compositions of this invention containing zinc salts and essential oils, have R-factors at or close to 1.0, thus indicating these formulas kill the biofilms about as rapidly as the standard mouthwash, Listerine® (amber), which has been shown clinically to be effective in preventing plaque and gingivitis.

EXAMPLE 8

ADHERENCE OF ZINC TO DENTAL PLAQUE

The human oral retention of zinc from mouthwashes containing zinc salts has been studied and reported in the literature. G. J. Harrap, et al., *Archs Oral Biol.*, vol. 29, No. 2, pp. 87–91 (1984). According to Harrap, zinc retained in the mouth gives visible fluorescence after rinsing with 8-hydroxyquinoline, and is especially evident on the tongue, cheek mucosa and dental plaque. This oral zinc concentration was markedly increased 1 hour after using 31 or 18 mM zinc phenolsuphonate, according to Harrap.

To determine how readily zinc adheres to dental plaque, the adherence of zinc to simulated plaque grown on steel wires was fluorimetrically measured. Increasing concentrations of zinc solutions were used in the test oral compositions.

After the simulated plaque is developed on the wires, it is then immersed in the oral composition to be tested, which is followed by a rinse. Thereafter, the plaque coated wires are immersed in a 0.01% solution of 8-hydroxyquinoline prepared by dissolving the 8-hydroxyquinoline in 100% ethanol. Twenty (20) ml of this solution were then brought q.s. up to the correct concentration.

Using $ZnCl_2$ at concentrations of 0.001%, 0.010%, 0.025%, 0.050% and 0.100% in a base oral composition identical to Example 2, we found using an excitation light of 360 nm and emission at 530 nm or 590 nm, that at concentrations as low as 0.001% (w/v) fluorescence from zinc was detectable in dental plaque and the amount of fluorescence increased with increasing zinc concentration. These results establish that zinc adheres to dental plaque at extremely low levels, and that the amount of zinc retained is a function of the quantity of zinc supplied to the mouth.

The scientific evidence presented herein demonstrates that low concentration zinc solutions can effectively substantially reduce the evolution of VSC in vitro; that zinc present in mouthwash compositions can effectively prevent or reduce the development of oral malodor over a period of several hours in vivo; that zinc chloride solutions prevent or inhibit the development of VSC's overnight in vivo, thus leaving the breath feeling clean in the morning; and that even at low zinc concentrations, zinc adheres to dental plaque, thus providing the opportunity to inhibit the growth of plaque or calculus and thereby limiting the development of gingivitis or periodontal disease. However, as demonstrated by the R-factor assessment, the mere presence of a zinc salt in an oral composition may not be sufficient to prevent or limit development of plaque or gingivitis.

EXAMPLE 9

CONSUMER EVALUATION

In addition to effectively eliminating and preventing the recurrence of malodors, an oral composition must be acceptable to users. It should have a pleasant taste, and otherwise be organoleptically acceptable. As noted previously, oral compositions containing zinc salts have frequently been judged to have an unpleasant metallic or astringent aftertaste.

Mouthwash compositions containing zinc salts, menthyl succinate, and the four Listerine® essential oils were subjected to an evaluation by twelve panelists. All oral compositions tested contained 0.04% menthyl succinate and 0.1% zinc chloride. The only difference among the versions tested was the flavoring agents. The following three flavors were tested: Citrus-Mint, Mint, and Spice-Mint After home use, subjects reported the following sensations for the mouthwash prototypes: Clean; refreshing/cooling; with a bite/burn like Listerine®; pleasant aftertaste; sweet aftertaste; slick feeling on teeth; tightening along the gum line.

Overall, one of the twelve panelists reported that all the flavors had a drying, metallic aftertase. This is seen as a very positive result since unmasked zinc compositions are frequently unacceptable because thy taste too metallic and/or astringent.

EXAMPLE 10

CONSUMER EVALUATION

Oral compositions formulated according to Example 3 above, with and without mentyl succinate, were tested by eight panelists. Six of the eight panelists reported that the compositions with menthyl succinate tasted less astringent or metallic; one panelist reported the composition formulated with menthyl succinate was more astringent or metallic and one panelist could not tell the difference. These strong directional results in favor of compositions formulated with menthyl succinate further support the advantage of using menthyl succinate to mask the astringent/metallic tast of zinc in an oral composition.

What we claim is:

1. An oral composition containing a zinc salt present in an amount of about 0.05% to about 0.4% by weight with respect to said oral composition and a coolant selected from the group consisting of monomenthyl succinate, alkali metal salts of monomenthyl succinate, alkaline earth metal sales of monomenthyl succinate and mixtures thereof present in an amount of about 0.001% to about 0.4% by weight with respect to said oral composition.

2. The oral composition according to claim 1 further comprising thymol, and one or more essential oils selected from the group consisting of eucalyptol, menthol and methyl salicylate.

3. The oral composition according to claim 2 wherein the zinc salt is present in an amount of about 0.05% to about 0.4%, thymol is present in amounts from about 0.001% to about 0.35% w/v, eucalyptol is present in amounts of from about 0.001% to about 0.20% (w/v), menthol is present in amounts from about 0.001% to about 0.35% w/v and methyl salicylate is present in amount of from about 0.001% to about 0.30% w/v.

4. The oral composition according to claim 1 wherein the coolant is selected from the group consisting of monomenthyl succinate, monomenthyl sodium succinate, monomenthyl potassium succinate, monomenthyl lithium succinate, monomenthyl calcium succinate, monomenthyl magnesium succinate, monomenthyl barium succinate and mixtures thereof.

5. The oral composition according to claim 1 further comprising a second coolant compound selected from the group consisting of menthol, carboxamides, ketals, menthyl acetate, menthyl lactate, 3-menthoxypropane-1,2 diol and mixtures thereof.

* * * * *